US008626526B2

(12) United States Patent  
Lemke et al.

(10) Patent No.: US 8,626,526 B2
(45) Date of Patent: Jan. 7, 2014

(54) SYSTEM AND METHOD FOR A HEALTHCARE COMMUNICATION FRAMEWORK

(75) Inventors: Kai Lemke, Schwetzingen (DE); Ali Gerhard Tafazzoli-Yazdi, Heidelberg (DE); Mark Anthony Oshifeso, Regensdorf (CH); Wolfram Puechert, Speyer (DE)

(73) Assignee: SAP AG, Walldorf (DE)

( * ) Notice: Subject to any disclaimer, the term of this patent is extended or adjusted under 35 U.S.C. 154(b) by 889 days.

(21) Appl. No.: 12/416,599

(22) Filed: Apr. 1, 2009

(65) Prior Publication Data

US 2010/0088110 A1  Apr. 8, 2010

Related U.S. Application Data

(60) Provisional application No. 61/103,145, filed on Oct. 6, 2008.

(51) Int. Cl.
*G06Q 10/00* (2012.01)

(52) U.S. Cl.
USPC .................................. 705/2; 705/3; 707/100

(58) Field of Classification Search
USPC ............................................................ 705/2
See application file for complete search history.

(56) References Cited

U.S. PATENT DOCUMENTS

| 7,275,220 B2* | 9/2007 | Brummel et al. ............. 715/804 |
| 2005/0228808 A1* | 10/2005 | Mamou et al. ................ 707/100 |
| 2010/0131962 A1* | 5/2010 | Zakonov ....................... 719/315 |

* cited by examiner

*Primary Examiner* — Hiep V Nguyen
(74) *Attorney, Agent, or Firm* — Kenyon & Kenyon LLP

(57) ABSTRACT

A computer-implemented method is described for asynchronous service-based communication. The method includes steps of generating events in an application layer of a computer software system, storing the generated events in a database table and scanning the database table by a process of a healthcare communication framework (HCF) at a time after the generated events are stored. The computer software system can run on a computer implementing the HCF and the generated events targeting service operations exported by another software system. During each scan the process is configured to group the events in the database table into packages based on a respective context of each event. For each package: consistency is checked for each event contained in the package, a consolidation logic is applied to consolidate events contained in the package, services operations associated with each event not being consolidated are found, and the service operations are invoked asynchronously.

20 Claims, 7 Drawing Sheets

Out Bound Process 400

Event Table 300

| Field | Description |
|---|---|
| MANDT | Client |
| EGUID | GUID for Event |
| LUWID | ID of originating business transaction LUW |
| TA | Name of originating transcation |
| TIMESTAMP | Time of event |
| User | User |
| APPLK | Owner of Event |
| EVENT | Eventcode |
| EINRI | text |
| PATID | text |
| CASEID | text |
| KEY1 | Supplementary text |

FIG. 3

SYSTEM AND METHOD FOR A HEALTHCARE COMMUNICATION FRAMEWORK

CROSS-REFERENCE TO RELATED APPLICATIONS

This application claims priority to U.S. Provisional Patent Application No. 61/103,145, filed Oct. 6, 2008, entitled "Healthcare Communication Framework," which is herein incorporated by reference in its entirety.

BACKGROUND

Health care institutions (e.g., hospitals, clinics, doctor's offices) may have multiple computer software systems to provide a variety of services. For example, a hospital may use an administrative system for admission of patients. The administrative system may facilitate taking and managing information such as patient name, insurance information, etc. The hospital may have a billing system to generate invoices and send bills to insurance companies, and a lab system to manage diagnostic tests. Sometimes, the services provided by another system may be needed. For example, the administrative system may need to invoke services provided in the billing system to generate bills and services provided in the lab system to schedule diagnostic tests. There is a need to integrate diverse systems, such as an administrative system, a billing system and a lab system, by a communication framework.

BRIEF DESCRIPTION OF THE DRAWINGS OF THE EXAMPLE EMBODIMENTS

FIG. 3 shows one example of data fields of a runtime events table according to one example of the present invention.

DETAILED DESCRIPTION OF THE EXAMPLE EMBODIMENTS

Embodiments of the present application implement event-driven asynchronous communication between different software systems. Events may be pre-defined and generated at runtime by software systems in accordance with business needs (e.g., admission of a patient, input/modification of insurance information for a patient, etc.). In one embodiment, events may be persisted in a database such that subsequent processing steps may be performed at a later time by scanning entries in the database. For example, an outbound processor may be implemented to periodically check the database and process events accumulated since the last check. The subsequent processing steps may include, but are not limited to, finding a service operation targeted by a respective event, filling context information for the service operation, and calling a proxy of the service operation. These steps will be described in detail below. The outbound processor may be scheduled to execute in the background (e.g., without user interface and/or user interaction). In one or more embodiments, users may define and/or modify service operations without modification to the framework of the system. The communication framework in accordance with embodiments of the present invention may be termed a healthcare communication framework (HCF).

Figure 1:
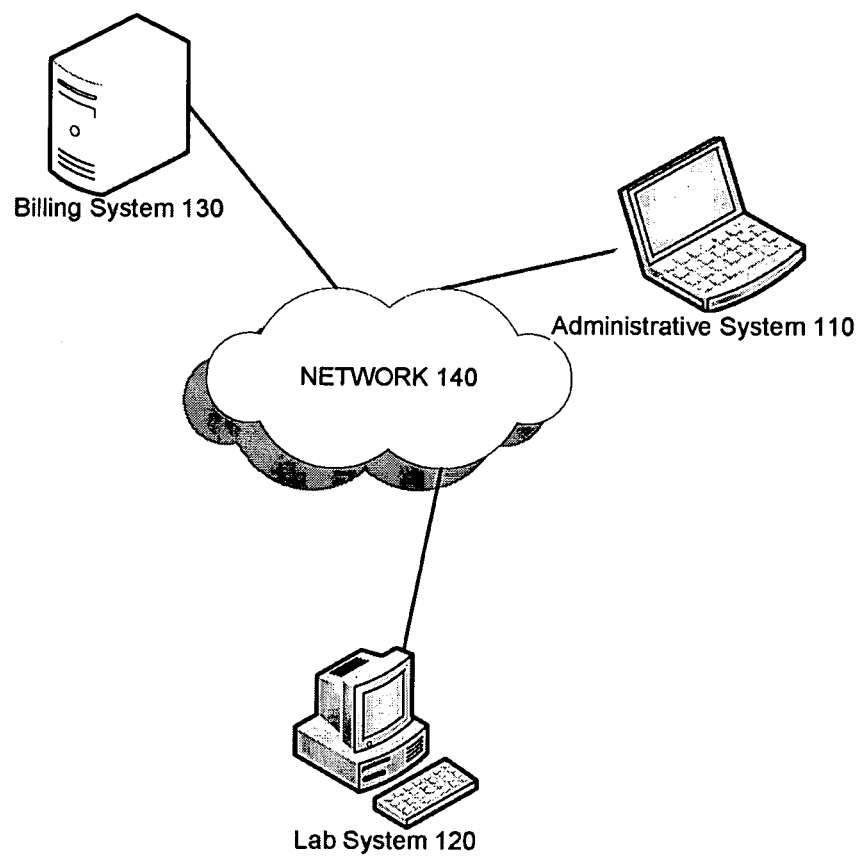
FIG. 1 shows example systems for a health care institution according to one example of the present invention.

FIG. 1 shows example systems of a health care institution 100 according to one example of the present invention. The health care institution 100 have multiple computer software systems to provide a variety of services. One of such software systems may be an administrative system 110, which provides information management relating to administrative tasks (e.g., admission/discharge of a patient). The health care institution 100 may further include a lab system 120. The lab system 120 may facilitate diagnostics tests to be performed by a laboratory (e.g., blood testing). The health care institution 100 may also include a billing system 130 to generate invoices and send bills to insurance companies. The administrative system 110, lab system 120 and billing system 130 may be connected via a network 140, such that one system may interact with another system to perform a certain function. For example, the administrative system 110 may need to invoke services provided in the lab system 120 and/or billing system 130. In one embodiment, one or more of the systems of the health care institution 100 may need to communicate with external systems (e.g., a system of an insurance company).

One way of communication between diverse systems may be synchronous communication. Synchronous communication establishes connections between different participating systems in a synchronized manner. In this manner, systems participating in the communication must be present during the whole time period the communication is in progress. Once synchronous communication is established, the initiating system will resume its own execution only after the synchronous communication is completed. That is, the initiating system has to complete the communication with other systems before continue its own execution. Thereby, synchronous communication may block execution of the initiating system. If a subsequent change is made in the initiating system, the change may cause the initiating system to start another round of synchronous communication. Resources (e.g., bandwidth of the network) may be spent by recurring communications between different systems running on different computers. For example, an update to a patient's information in the administrative system 110 may cause the administrative system 110 to invoke services provided in the lab system 120 and/or billing system 130, thus a new round of synchronous communication is needed.

In one embodiment, communication between various systems 110, 120 and 130 may be implemented as remote procedure calls. That is, each system may export certain procedures to represent service operations that can be called by another system. The remote procedure calls may be facilitated by proxies. Each proxy presents a corresponding remote procedure to be called by a calling system. The procedure calls may be performed synchronously and/or asynchronously. For example, a patient information may be transmitted from the administrative system 110 to the billing system 130 when a bill for the patient needs to be generated. That is, the administrative system 110 may initiate a remote procedure call synchronously to invoke the service operation in the billing system 130 to generate the bill. Alternatively, the administrative system 110 may generate a request (e.g., an event) and submit the request to a system or queue to be fulfilled later (e.g., asynchronously). For example, the bill may be generated at night when there is less network communication and less computing activity by computers running the billing system 120.

In one embodiment, asynchronous communications may be implemented for certain types of remote procedure calls and synchronous communications may be implemented for other types. A system designer may define what types of remote procedure calls should be implemented as synchronous or asynchronous. It should be noted that the administrative system 110, lab system 120 and billing system 130 are exemplary systems of the health care institution 100. The health care institution 100 may include other systems not shown in FIG. 1 and may include systems less than shown in FIG. 1.

Figure 2:
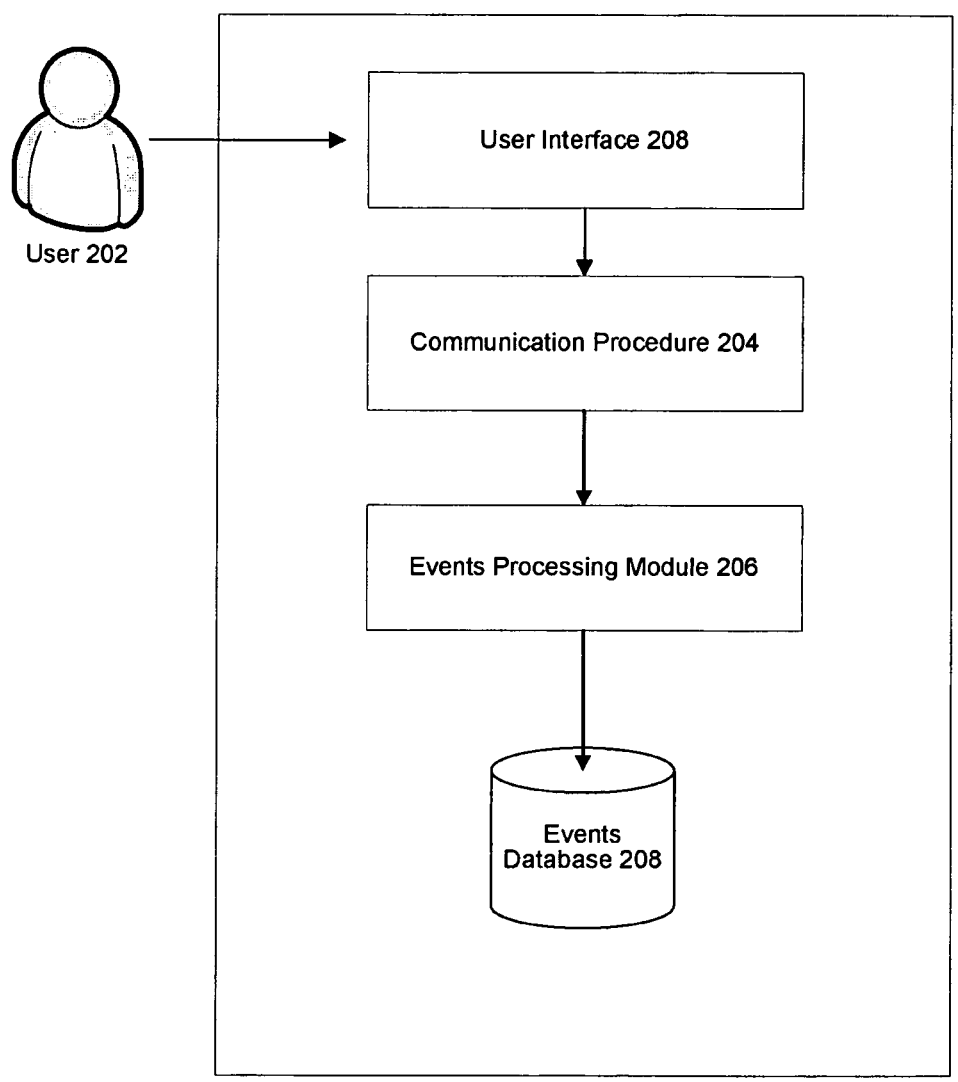
FIG. 2 shows one example of high level components included in an eventing framework according to one example of the present invention.

FIG. 2 shows one example of high level components included in an eventing framework 200 according to one example of the present invention. Eventing may cover detection of events and supply of further processing steps of the events. The eventing framework 200 may be implemented by any of the computer software systems (e.g. administrative system 110, lab system 120 or billing system 130). The eventing framework 200 may include a user interface 208, a communication module 204, an events processing module 206 and events database 208. A user 202 may interact with the user interface 208. The interaction may cause events to be generated (e.g., generating a bill for a patient). The communication module 204 may implement functions that collect events and call related function modules. In one embodiment, the communication module 204 may be implemented as a "virtual" communication module. For example, the "virtual" communication module may perform various exchange data interface (EDI) procedures. They may provide a way to establish connections between an information system (e.g., administrative system 110) and a data exchange infrastructure (e.g., exchange infrastructure 632 shown in FIG. 6).

The events processing module 206 may be invoked by the communication module 204 for post processing of events that have been triggered for one business transaction (e.g., entry of a patient's information or a request to generate a bill by the user 202). The events processing module 206 may aggregate events by keeping the order by which events are generated and writing the events into the events database 208. In one embodiment, the database 208 implements a runtime events table to store the events written by the event processing module 206. In one embodiment, events may be collected within the database 208 as persistent events.

FIG. 3 shows one example of data fields of a runtime events table 300 according to one example of the present invention. In one embodiment, the runtime events table 300 may include data field "MANDT" for clients (e.g., each representing an enterprise with a runtime system), "EGUID" for a globally unique identifier for the event, "LUWID" for an identifier of the originating business transaction Logical Unit of Work (LUW), "TA" for name of the originating transaction, "TIMESTAMP" for the time the event is generated, "User" to identify the user of the system generating the event, "APPLK" for the owner of the event, and "EVENT" for a code identifying the eventcode. The runtime events table 300 may further include data fields with text that describes an institution (e.g., EINRI), a patient identifier (e.g., PATID), and case identifier (e.g., CASEID). The runtime events table 300 may also include supplementary text fields to describe additional aspects of a respective event, such as, but not limited to, data field Key 1.

Events stored in the runtime events table 300 may be processed at a later time (e.g., periodically, or a designated later time) by an outbound processor. If an error occurs during the process, an error may be recorded in an event errors table. The event errors table may be similar to the runtime events table 300 and contains data fields and information stored in the runtime events table 300. Additionally, the event errors table may store error information to facilitate diagnosis of the errors.

Figure 4:
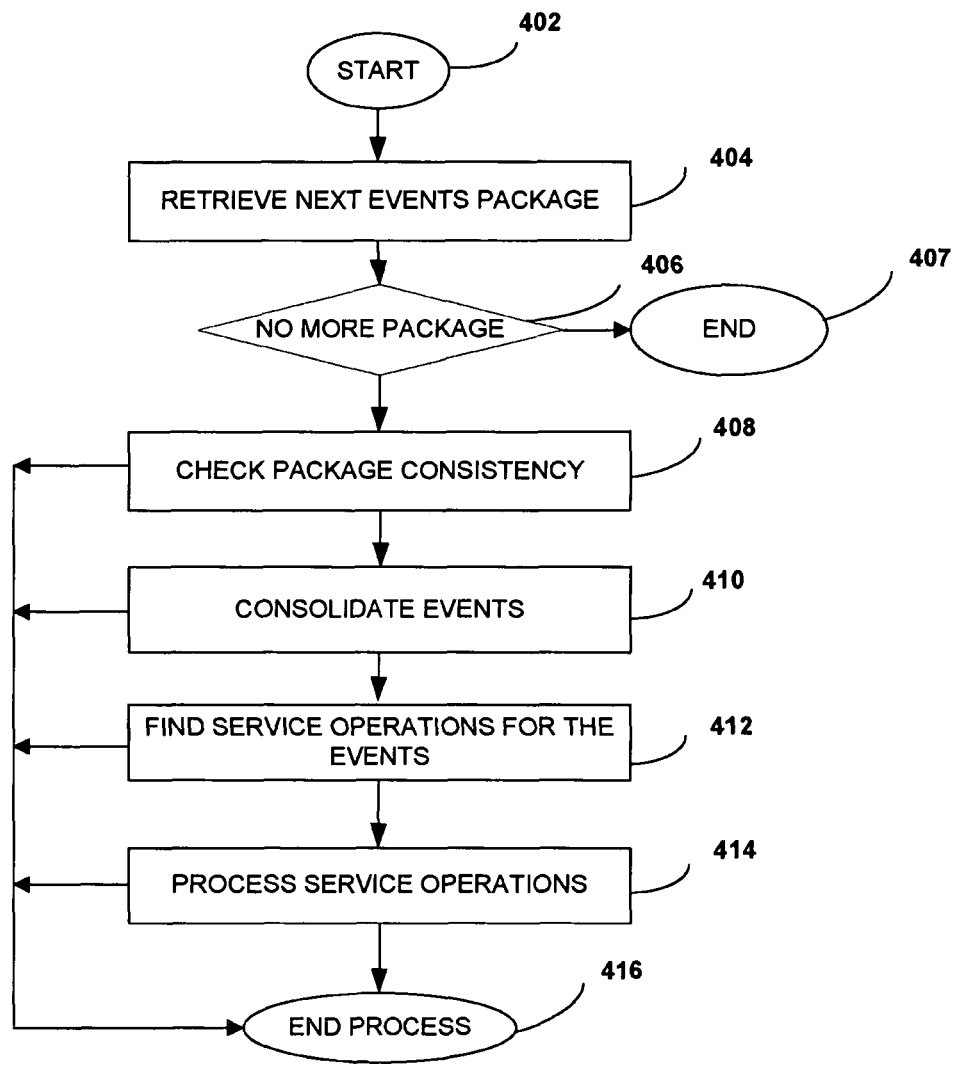
FIG. 4 shows one example of an out bound process according to one example of the present invention.

FIG. 4 shows one example of an out bound process 400 according to one example of the present invention. The out bound process 400 may be implemented by any of the software systems of the health care institution 100 that use asynchronous communication. In one embodiment, the out bound process 400 may be scheduled to run periodically as a back-end computer service. When executed, the out bound process 400 may process events accumulated in the runtime events table 300 and event errors table between the last run and the current run. If an error occurs during execution of the out bound process 400, the error may be written to the event errors table. In one embodiment, an administrator may be notified of the error by an alert, which will be described in detail later. Further, if the same error is found again during the next run of the out bound process 400 (e.g., because the administrator has not yet fixed the error), the alert may be suppressed.

The out bound process 400 may start with step 402 and continue to step 404. At step 404, the out bound process 400 may try to retrieve an events package. Events in the runtime events table 300 and the event errors table are packaged in to events packages according to the context of each event. In one embodiment, an event manager may be implemented. The event manager may build events packages based on a predetermined criteria. Each events package may be processed as a unit. That is, all events contained in one package may be processed together. For example, events may be grouped in one events package for one patient based on a patient context. The patient context may ensure that all events that might be relevant for later consolidation and may be written to the event errors table are contained in one package. The consolidation of events are described in detail below.

In one embodiment, events stored in both the runtime events table 300 and the event errors table need to be processed in chronological order. In case of any error occurring during the process, any subsequent related events may also be put in the event errors table. In one embodiment, any subsequent events with the same PATID may be related to same patient and may be treated as related events. For events without patent context, such as a patient identifier, a pre-defined criteria may be used to group events. The same pre-defined criteria may also be used for consolidation of events when processing events packages.

At step 406, the out bound process 400 may determine whether the retrieval step 404 is successful. If no package can be retrieved and thus no more packages are to be processed, the out bound process 400 may end at step 407. If a package is retrieved, the out bound process 400 continues to step 408.

At step 408, the out bound process 400 may check consistency for each event contained in the events package being processed. For example, the step 408 may check whether relevant patient context is provided. If an error occurs during the step 408, the step 408 may raise an error identified as basic consistency error and continue to step 416, which may store the error in the event errors table. In one embodiment, the events package may include a field identifying the last error that has occurred. This field of last error may contain error information that is existent to an event in the event errors table. Thus, this information in an events package may suppress multiple alerts for the same error. If no error occurs, the out bound process 400 may continue to step 408.

At step 410, the out bound process 400 may consolidate events contained in the current events package. In one embodiment, the out bound process 400 may implement a consolidation logic. The consolidation logic may be applied to each event in the events package to determine if the respective event may be consolidated with another event in the events package. Consolidation may be implemented as aggregation of events that were triggered between the last and current run of the out bound process 400, and may reduce and/or eliminate redundant service operation calls during the out bound process 400. The events package may contain supplementary information reflecting the status of the consolidation steps. For example, the events package may have a field identifying whether an event has been consolidated with another event and the other event's identifier. The events package may further include a field about a status identifying whether a respective event is no longer the object of event processing steps of the out bound process 400. The status may be set to "processed", when the event has been consolidated. The out bound process 400 may skip all events with a status of "processed" for further processing steps. However, the consolidated events are not deleted from the runtime events table yet because in case of error scenarios, they also have to be inserted in the event errors table.

In one or more embodiments, consolidation is implemented to reduce/eliminate redundant service operation calls. The redundant service operation calls may be identified by certain patterns. Each pattern may use business objects and context to distinguish service operation calls. The term business object is described below. Context may be patient context, e.g., the same patient as identified by a patient identifier.

In one pattern, for example, two events may have identical service operation calls thus the two events may be consolidated. In this case, the second event may be marked as "processed" and only one service operation call is performed. The pattern may be identified by the same business object, the same context and the same action.

In another exemplary pattern, a change service operation call may follow a preceding creation service operation call. For example, after a patient's information has been entered into the administration system 110, the patient's information has been subsequently modified. An event may be stored in the runtime events table 300 for initial entry of the patient's information, and a subsequent event may be stored for the subsequent modification. The two events may have the same patient context and thus may be consolidated (e.g., modify information of the initial event with change from the subsequent event). The subsequent event may be treated as already processed (e.g., marking it as "processed"). The out bound process 400 may skip the subsequent event in later steps (e.g., for locating and calling the service operation). This exemplary pattern may be identified by the same business object, the same context and a creation action plus a change action.

In a further exemplary pattern, an event may cancel a service operation following a preceding event to create the service operation (e.g., canceling generation of a bill for a patient). The consolidation may cancel the creation service operation call and the out bound process 400 will invoke no service operation calls for these two events. This further exemplary pattern may be identified by the same business object, the same context and a creation action plus a cancel action.

If an error occurs during the step 410, the step 410 may raise an error identified as a consolidation error and continue to step 416, which may store the error in the event errors table. The error information may be stored in the last error field of the events package before being processed in step 416. If no error occurs, the out bound process 400 may continue to step 412.

At step 412, the out bound process 400 may find service operations for the events contained in the events package being processed. In one embodiment, the out bound process 400 may find service operations for each event in the events package with a status not set to "processed." The service operations for each event may be determined by pre-defined configurations. The configurations to associate operation services with events may be stored in configuration information database tables or configuration files. During the step 412, if an event is marked as "processed" in the status field, the event may be skipped by the step 412 and no service operations will be searched for the event.

In one embodiment, the events package may contain supplementary information reflecting the status of the finding service operation steps. For example, the events package may include a field for service operations. One or more service operations may be associated with one event. That is, each event may cause one or more service operations to be invoked. The service operations may be implemented as a nested structure for each event. The nested structure may contain the service operations that are found for the given event. This field for service operations may be filled when the previous step 410 (e.g., consolidation) and current step 412 (e.g., service operation finding) are successful. If an error occurs during the step 412, the step 412 may raise an error identified as a service operations finding error and continue to step 416, which stores the error in the event errors table. The error information may be stored in the last error field of the events package before being processed in step 416. If no error occurs, the out bound process 400 may continue to step 414.

At step 414, service operations identified for each event in step 412 are invoked. In one or more embodiments, the out bound process 400 may implement procedures to fill in context information of each service operation and call respective proxies of the service operations. In one embodiment, invocation of service operation may be performed asynchronously, e.g., using message queues.

Embodiments of the present invention may use message queuing to provide an asynchronous communication. Message queuing is an asynchronous communications protocol. Using message queues, senders and receivers of messages do not need to interact with the message queues at the same time. Messages placed onto a queue are stored until the recipient retrieves them from the queue. Some message queues have set limits on the size of data that can be transmitted in a single message but some others do not. Some implementations of message queues allow the passing of messages between different computer systems, potentially connecting multiple applications and multiple operating systems. These message queuing systems typically provide enhanced resilience functionality to ensure that messages do not get "lost" in the event of a system failure. Examples of commercial implementations of this kind of message queuing software (also known as Message Oriented Middleware) include IBM's WebSphere MQ (formerly MQ Series), Oracle Advanced Queuing (AQ) within an Oracle database, and Microsoft's MSMQ. The Java standard called Java Message Service has, associated with it, a number of implementations, both proprietary and free software. Embodiments of the present invention may use any existing message queuing systems or may develop custom message queuing systems.

If an error occurs during the step 414, the step 414 may raise an error identified as a process service operations error and continue to step 416, which stores the error in the event errors table. The error information may be stored in the last error field of the events package before being processed in step 416. If no error occurs, the out bound process 400 may continue to step 416 without raising an error.

At step 416, the out bound process 400 may perform clean up tasks before ending the process. In one embodiment, the step 416 may raise an alert for errors raised during any of previous steps. Also, the step 416 may store the errors in the event errors table. If there are no errors, the step 416 may delete entries in the events table because the current run successfully processed scanned events from the events table. If events from event errors table are also processed without error, corresponding entries in the event errors table may also be cleaned. In one embodiment, the out bound process 400 may implement transactions to protect data integrity in the step 416. For example, a transaction may be started as soon as the step 416 starts, if certain work has been performed before encountering the error, the work may be rolled back. The transaction may only be committed when the step 416 has executed successfully. Further, changes to either runtime events table and event errors table may also be wrapped around by the transaction and occur only after a successful execution of other functions in step 416.

In one or more embodiments, the out bound process 400 may skip integrity checks. Integrity checks normally make sure context information or data supplied to proxies conform to the remote procedure's requirement. A layered implementation of the software system may be implemented and the integrity checks may be implemented at an application layer not at the out bound process 400. However, the out bound process 400 is prepared to handle errors for each processing step. Thus, an integrity check framework may be added to the health care communication framework if needed. Further, in one embodiment, error situations that occur during out bound process 400 may be forwarded using one generic alert implementation. More complex alert framework may be employed if more complex errors than mere technical errors are anticipated.

Figure 5:
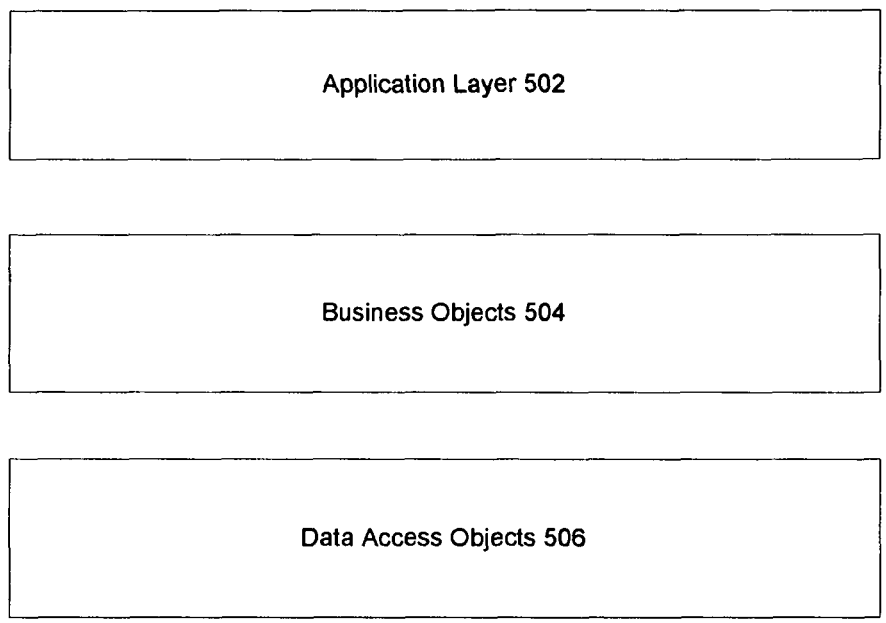
FIG. 5 shows one example of a business object model in accordance with one exemplary embodiment of the present invention.

FIG. 5 shows one example of a business object model 500 in accordance with one exemplary embodiment of the present invention. The business object model may comprise an application layer 502, a business objects layer 504 and a data access objects layer 506. The application layer 502 may include user interface elements and modules that are responsive to user interactions. Events may be generated in the application layer 502 and stored in the runtime events table. The business objects layer 504 comprises a plurality of business objects. The business objects may represent the entities in the business domain for an HCF (e.g., a patient, a customer, etc). These business objects may be sometimes called domain objects; a domain model represents the set of domain objects and the relationships between them. A business object (e.g., a patient object) often encapsulates all of the data and business behavior associated with the entity that it represents. Business objects do not necessarily need to represent objects in an actual business, though they often do. They can represent any object related to the HCF for which a system developer may define any business logic. The business object model 500 may be implemented in one or more object oriented programming languages (e.g., Java, C++).

The business objects may access data stored in any underlying database through the data access objects (DAO) layer 506. The DAO layer 506 provides an abstract interface to an underlying database or persistence mechanism. It provides data specific operations without exposing details of the database. This isolation separates the concerns of what data accesses the HCF needs, in terms of business objects and data types, and how these needs can be satisfied with a specific DBMS, database schema, etc. In one or more embodiments, the DAO layer does not contain any control for transactions. That is, data access objects may not implement "commit" for transaction and leave the transaction control to the business objects in the layer 504.

Errors may occur when a data access object is accessing data. In this case, one or more exceptions may be generated (e.g., thrown) in the DAO and propagated to the caller (e.g., a business object invoking the DAO). The exceptions may be of technical or business nature. For example, technical exceptions may be caused by customizing inconsistencies, inactive Data Dictionary (DDIC) and invalid parameters. Business exceptions may be errors caused by invalid application programming interface (API) calls (e.g., trying to access information for a non-existent patient). A business exception may be propagated by raising an alert to an administrator.

Errors and exceptions have been mentioned above. In one embodiment, problematic situations may be grouped into exceptions, errors, and conflicts. Exceptions may indicate that some unexpected condition has occurred which cannot be fixed by an end user. They might be fixed by the system administrator. Exemplary exceptions may be database inconsistencies, invalid customizing settings, code errors (e.g. invalid parameters passed to a method), authorization problems (if they cannot be corrected by the user), unexpected error situations in the proxy coding before and after the business logic calls. Errors may be problems that can be solved by a user, e.g., correcting the input data or by doing the action some time later, data inconsistencies with a (incoming) message (e.g. unknown service operation code). Conflicts may occur when there are process inconsistencies with a (incoming) message, e.g., choreographic errors.

The business object model 500 may be implemented across systems with each system exporting services to be invoked by other systems. As described above, service operations implemented in another system may be invoked through messaging queues. This service oriented architecture (SOA) using asynchronous messages may result in loose coupling of systems. Further, the SOA may use no cross system transactions (as DB LUW) and may use no cross system locks. This may lead to an optimistic approach where each system is responsible for its own process steps. Results of the steps are published via messages (e.g., invocation or acknowledgement). This also means that there are limited checks for the invoked systems, whereas many checks are done in the invoking system. In one or more embodiments, forward recovery may be chosen for resolution strategies (e.g., exception, error or conflict situations), which might come up in a subsequent system since rollback of a LUW is no longer possible (due to loose coupling). That is, errors at the receiver-side are to be handled independently from the sender.

Figure 6:
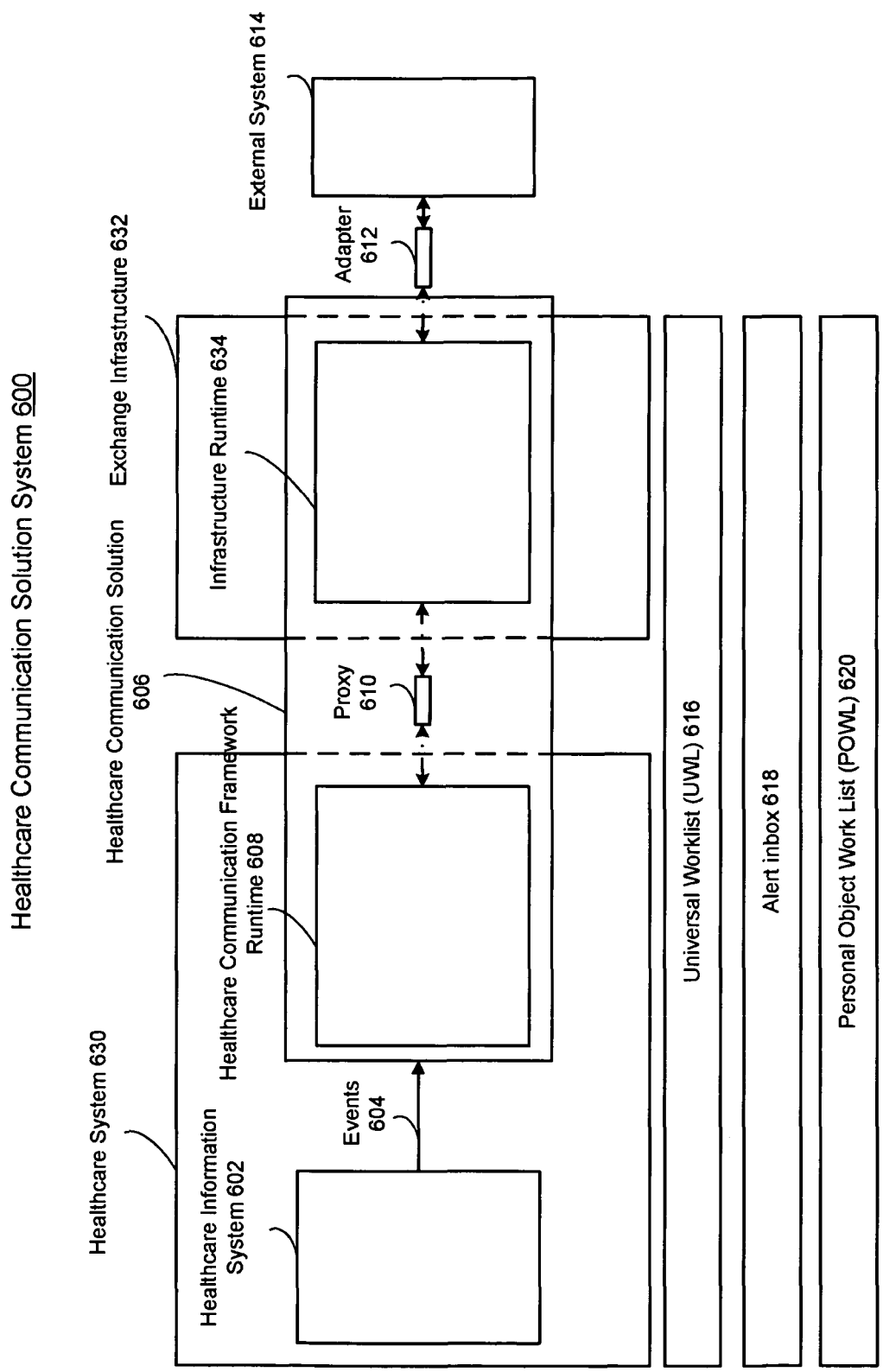
FIG. 6 shows one healthcare communication solution system in accordance with one example embodiment of the present invention.

FIG. 6 shows one healthcare communication solution system 600 in accordance with one example embodiment of the present invention. The healthcare communication solution system 600 may comprise a healthcare system 630, an exchange infrastructure 632 and an external system 614. The healthcare system 630 (e.g., an administrative system) may comprise a healthcare information system 602 and a healthcare communication framework (HCF) runtime 608. The exchange infrastructure 632 may comprise an infrastructure runtime 634. The HCF runtime 608 and infrastructure runtime 634 may be components of a healthcare communication solution 606 that spread beyond one single computer system. The external system 614 may be a computer system of a business partner (e.g., a health insurance company) and may run a different computer hardware/software system. In one embodiment, more than one external system may be included in a healthcare communication solution system. The healthcare communication solution system 600 may further comprise a universal worklist (UWL) 616, an alert box 618 and a personal object work list (POWL) 620.

The healthcare information system 602 may comprise the application layer 502 described above in FIG. 5 and may raise events 604. The events 604 may be transmitted to the HCF runtime 608 in the order that they are raised. The HCF runtime 608 may process the events in the order they are received. Events 604 may be related to service operations provided in another system (e.g., a billing system not shown) and those service operations may need to be invoked in the same order on a proxy 610.

In one embodiment, to ensure a proper sequence for invoking the service operations, a named queue may be used. Instead of all messages sharing one message queue, multiple queues with unique names may be created. Thus, each message may be put into a specific named queue based on the message's target system, target service operation (e.g., a specific remote procedure), or a message context (e.g., a patient ID). With named queues, the HCF outbound proxy calls (e.g., outbound messages) may be enhanced to allow a strict sequencing (e.g., exactly once in order (EOIO)). In one embodiment, the sequencing context may be based on a patient ID. If a patient ID is available, the patient ID may be used for a queue name to ensure all service operations related to the patient are put in one queue and EOIO may be strictly enforced. If a message has no patient ID, a named queue is not used for the message. The message may be delivered to queues managed by the proxy framework (e.g., proxy 610) to ensure exactly once (EO) delivery. However, the sequence for those services is not to be guaranteed. In one or more embodiments, the proxy 610 may create queues if there is no patient ID and HCF runtime 608 does not create named queues.

The exchange infrastructure 632 may also need to implement functions to ensure EOIO if EOIO is requested by the HCF runtime 608. In one or more embodiments, the infrastructure runtime 634 may further communicate with the external system 614 through an adapter 612. Thus, not only the infrastructure runtime 634 needs to perform the service operations in the sequence as set forth by the HCF runtime 608, it may further ensure messages sent to the external system 614 to be in that sequence. The adapter 612 may be required to be EOIO capable to facilitate the mission.

In one embodiment, the external system 614 may send messages to the HCF runtime 608. The messages may be termed inbound messages with regard to the HCF runtime 608. The inbound messages may be sent via the adapter 612 to the infrastructure runtime 634. The infrastructure runtime 634 may invoke service operations exported by the HCF runtime 608 via the proxy 610. Message queuing including named queues described above for the proxy 610 may also be used for the inbound messages as well. The external system 614 may also require EOIO behavior for inbound messages. To enforce the EOIO behavior, the adapter 612 may be required to be EOIO capable. Further, named queues may be required for invocation of service operations through the proxy 610.

If no error occurs and EOIO is used, then the inbound proxies at the proxy 610 will be called in the correct order. If an error occurs, then the sequence will only be guaranteed for subsequent errors, which may be caught by the business object model implemented by the healthcare communication solution system 600. In one embodiment, the first erroneous message will be persisted in a monitor in the exchange infrastructure 632. The follow-up messages may run into errors and also be persisted by the monitor. An administrator may be informed with an alert through the alert inbox 618 and he or she might restart the message at a later point in time. For example, if a service operation to create a patient object has an error and is not processed. A subsequent service operation to change the patient object may cause an exception to be raised in the HCF runtime 608, because the patient doesn't exist yet. So the subsequent message is not processed and will instead be put into the monitor. In one embodiment, messages like several change messages for the same patient might be processed not in the order the messages are generated.

HCF may be activated and/or deactivated at an institutional level. The HCF runtime 608 and the infrastructure runtime 634 only run when the HCF is activated. For example, configuration database may be used to store the HCF procedures pre-defined for the institution. The various HCF procedures run in the HCF runtime 608 and infrastructure runtime 634 when the HCF is activated. An administrator may activate the HCF procedures through a user interface menu (e.g., through the healthcare information system 602). In one embodiment, all exported operation services from either the HCF runtime 608 or infrastructure runtime 634 may be stored in one or more database tables.

In one embodiment, the HCF runtime 608 or infrastructure runtime 634 may implement exception handling by exception classes. These classes may have a hierarchical structure and have common attributes. Exceptions which are raised within HCF runtime 608 or infrastructure runtime 634 may be propagated to either the runtime caller or the inbound proxy 610 depending upon which is the caller. Succeeding actions may be taken at the caller. This may help restrain follow up actions taking place only at either of the two places. Follow up actions may include: raise an alert (e.g., send an alert to the alter inbox 618); send an error notification/message; write an application log entry; adjust the events table accordingly and any other action.

The healthcare communication solution system 600 may implement an alert management to provide a central notification system. The alert management may be accessed from all systems of the healthcare communication solution system 600 (except the external system). The healthcare communication solution system 600 may implement user functions/components for watching alerts. In one embodiment, the UWL 616 may be implemented, which may be a component coupled to a portal to display alerts to an administrator. In another embodiment, the alert inbox 618 may be implemented to receive alerts from the healthcare information system 602, HCF runtime 608, the proxy 610 and the infrastructure runtime 634. In a further embodiment, the POWL 620 may be implemented for data other than alerts (e.g., message history) to be shown to an administrator.

The alert management and the exception handling of the healthcare communication solution system 600 may provide different approaches for error handling. For example, one type of error may be resolved by the system administrator only. In one embodiment, an administrator may be informed about the exception by an alert (e.g., via the alert inbox 618, UWL 616, and/or POWL 620) and the administrator can log in the system to resolve it. One exemplary alert may be caused by faulty environment settings. The alert may comprise some text with an error description (and/or a call stack of the current procedure call context), link to the transaction for correcting the environment, and link to an monitor (leads directly to the concerned message).

Another type of error may be resolved by the end user only. An exemplary alert may be temporary errors, which couldn't be resolved by automatic retries or may be any unknown error. This kind of alert may also comprise some text with error description (and a call stack) and link to an monitor (leads directly to the concerned message). For the end users, only errors or conflicts may be relevant. These errors and conflicts may be defined by the business transactions implemented in the healthcare communication solution system 600. Such errors/conflicts may occur in the HCF runtime 608 during inbound or out bound processing or in the infrastructure runtime 634. From both locations, alerts may be thrown, which may contain descriptive texts and links to the related transactions.

Another type of error may be resolved first by end user, then by system administrator. In one embodiment, the link to the monitor may be provided only if the proxy 610 is involved In some situations, resolution of an error or conflict may need involvement from both the end user and the administrator. In such cases, an alert will be send first to the end user, who might fix the issue with business transaction(s). After successfully changing data in the transaction that caused the error/conflict, the end user may forward the alert to the administrator, who may then follow the link in the alert to the monitor and try to resend the message.

The alert management described above may also be applied if exception/error/conflict is caused by an inbound message initiated from the external system 614.

The healthcare communication solution system 600 may log its activities on request to support tracing and error finding for the initial setup of the system as well as during productive use. Logging may be switchable (active/inactive) at an institution level (e.g., via a database table entry and/or a user interface menu). Additionally, the log level can be set to different levels (e.g., just errors, errors and warnings or all messages). The HCF runtime logging may log activities from the HCF runtime 608. The exchange infrastructure 632 may offer additional logging and monitoring functionalities, e.g. to follow-up how a specific message was handled within infrastructure runtime 634. In one embodiment, the activities that may be logged in HCF runtime 608 are based on inbound or outbound processing (e.g., successful execution of a unit process, error occurring at a component). Logs may be stored in one or more database tables. User interface modules may be implemented to display logged data.

Figure 7:
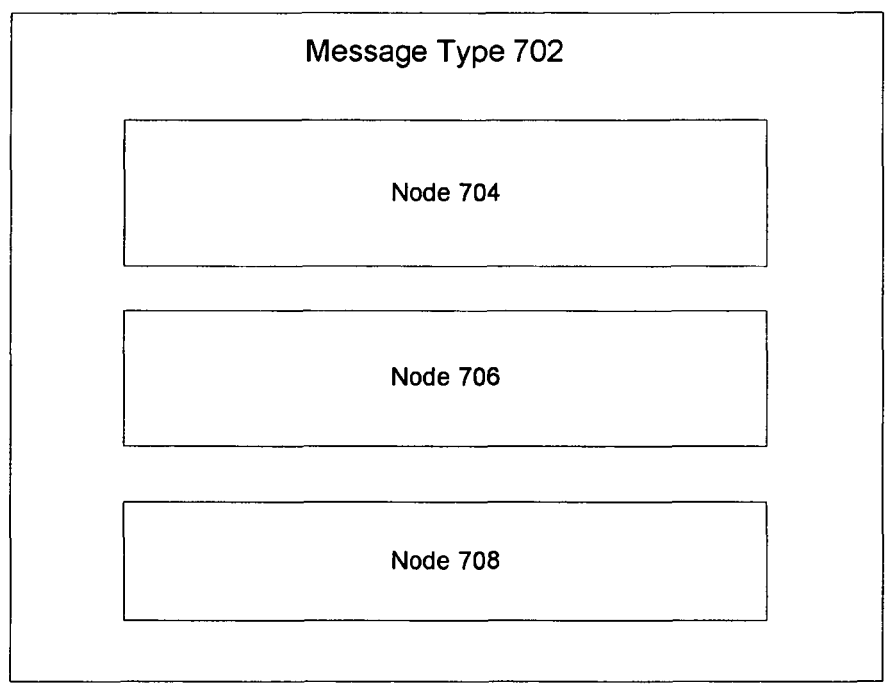
FIG. 7 shows one message layout in accordance with one example embodiment of the present invention.

FIG. 7 shows one message layout 700 in accordance with one example embodiment of the present invention. A message according the message layout 700 may comprise a message type 702. The message may further comprise one or more nodes, such as, nodes 704, 706 and 708. In one embodiment, the message type 702 may describe a complete structure of the message. The nodes 704, 706 and 708 may contain global data types (e.g., data types across systems at an institutional level) or are complex global data types themselves. For example, the node 704 may comprise general patient data, the node 706 may comprise data related to a case and the node 708 may comprise data related to encounter data. An encounter is a part of a visit in a healthcare provider institution, for example, admission, discharge and transfer.

In one embodiment, the data access objects in FIG. 5 may be used to access data represented by each node. One data access object may be defined to access data only for one node and from one data source. For example, patient data of node 704 may come from the healthcare information system 602 and external system 614. Two data access objects may be needed to access the patient data from two different data sources.

In one or more embodiments, acknowledgements to messages may be implemented. Acknowledgements may be requested by a message sender and the receiver(s) are to send requested information back to the sender. Acknowledgements may be useful for asynchronous messaging because unlike synchronous messaging, in which status information will be directly sent back, status information for asynchronous messaging is not available unless explicitly requested by the sender. Acknowledgments may differ from confirmations because acknowledgements are more of a technical nature and they may indicate that the processing of the message on the transport or application level has been successful. In contrast, confirmations may be outside the bounds of a transaction (e.g., confirming receipt of an order). In one embodiment, the HCF may supports various types of acknowledgements. For example, the default may be no acknowledgement (e.g., none). Alternatively, there may be system acknowledgement (e.g., by business objects), application acknowledgement (by application layer) and/or a combination of system and application acknowledgement.

The various computer systems described herein may each include a storage component for storing machine-readable instructions for performing the various processes as described and illustrated. The storage component may be any type of machine readable medium (i.e., one capable of being read by a machine) such as hard drive memory, flash memory, floppy disk memory, optically-encoded memory (e.g., a compact disk, DVD-ROM, DVD±R, CD-ROM, CD±R, holographic disk), a thermomechanical memory (e.g., scanning-probe-based data-storage), or any type of machine readable (computer readable) storing medium. Each computer system may also include addressable memory (e.g., random access memory, cache memory) to store data and/or sets of instructions that may be included within, or be generated by, the machine-readable instructions when they are executed by a processor on the respective platform. The methods and systems described herein may also be implemented as machine-readable instructions stored on or embodied in any of the above-described storage mechanisms.

Although the present invention has been described with reference to particular examples and embodiments, it is understood that the present invention is not limited to those examples and embodiments. Further, those embodiments may be used in various combinations with and without each other. The present invention as claimed therefore includes variations from the specific examples and embodiments described herein, as will be apparent to one of skill in the art.

What is claimed is:

1. A computer-implemented method for event-based asynchronous communication:
    generating events in an application layer of a computer software system, the application layer including user interface elements and modules that are responsive to user interactions, the computer software system running on a computer implementing a healthcare communication framework (HCF), the events being requests to asynchronously invoke service operations exported by another computer software system;
    storing the generated events in a database table; and
    scanning the database table by a process of the healthcare communication framework at a time after the generated events are stored, the process being run as part of the healthcare communication framework, wherein during each scan the process is configured to:
group the events in the database table into packages based on a predetermined criteria,
for each package:
check consistency for each event contained in the package, the consistency check determining whether relevant context information is provided in each event,
apply a consolidation logic to consolidate events contained in the package, wherein the consolidation logic determines whether multiple events invoke a respective service and combines later events of the multiple events into a first event of the multiple events to consolidate invocation of the respective service,
determine services operations associated with the consolidated events and each event not being consolidated, and
invoke the service operations asynchronously.

2. The method of claim 1, wherein the scanning process is run at fixed time intervals periodically.

3. The method of claim 2, wherein the predetermined criteria is patient identifiers.

4. The method of claim 3, wherein the consolidation logic uses patterns based on business object and context to perform consolidation.

5. The method of claim 4, wherein the patterns comprise same business object, same context and same action; same business object, same context and a creation action plus a change action; and same business object, same context and a creation action plus a cancel action.

6. The method of claim 4, wherein the consolidation logic mark each later event of the multiple events being consolidated as processed.

7. The method of claim 1, wherein to determine services operations associated with each event comprises filling a field corresponding to a respective event in the package with a nest structure, the nested structure containing service operations to be invoked for the respective event.

8. The method of claim 1, wherein to invoke the service operations asynchronously comprises:
generating a respective message for each service operation;
filling nodes of the respective message with data to be used by the service operation;
placing the message in a message queue.

9. The method of claim 8, wherein to invoke the service operations asynchronously further comprises processing a message from the message queue by invoking the service operation on a proxy representing the service operation.

10. The method of claim 8, wherein the message queue is a named queue.

11. The method of claim 10, wherein the healthcare communication framework ensures invocation on service operations exactly once in order (EOIO).

12. The method of claim 10, wherein healthcare communication framework comprises a personal object work list to display message histories on a display device.

13. The method of claim 12, wherein the process implements exception handling that stores error raised by any steps of the process into an errors table.

14. The method of claim 1, wherein the healthcare communication framework is activated at an institutional level.

15. The method of claim 14, wherein the process scans the errors table as well as the events table at fixed intervals.

16. The method of claim 15, wherein each alert in the alert management comprises a text description and a call stack.

17. The method of claim 1, wherein the healthcare communication framework stores the operation services exported by software systems in database tables.

18. The method of claim 1, wherein the healthcare communication framework comprises an alert management that provides a central notification system.

19. A system for event-based asynchronous communication, comprising:
a memory;
a processor configured to execute machine codes capable of:
generating events in an application layer of a computer software system, the application layer including user interface elements and modules that are responsive to user interactions, the computer software system running on a computer implementing a healthcare communication framework (HCF), the events being requests to asynchronously invoke service operations exported by another computer software system;
storing the generated events in a database table; and
scanning the database table by a process of the healthcare communication framework at a time after the generated events are stored, the process being part of the healthcare communication framework, wherein during each scan the process is configured to:
group the events in the database table into packages based on a predetermined criteria,
for each package:
check consistency for each event contained in the package, the consistency check determining whether relevant context information is provided in each event,
apply a consolidation logic to consolidate events contained in the package, wherein the consolidation logic determines whether multiple events invoke a respective service and combines later events of the multiple events into a first event of the multiple events to consolidate invocation of the respective service,
determine services operations associated with the consolidated events and each event not being consolidated, and
invoke the service operations asynchronously.

20. A non-transitory computer-readable medium including instructions adapted to be execute to implement a method for event-based asynchronous communication, the method comprising:
generating events in an application layer of a software system, the application layer including user interface elements and modules that are responsive to user interactions, the software system running on a computer implementing a healthcare communication framework (HCF), the events being requests to asynchronously invoke service operations exported by another software system;
storing the generated events in a database table; and
scanning the database table by a process of the healthcare communication framework at a time after the generated events are stored, the process being part of the healthcare communication framework, wherein during each scan the process is configured to:
group the events in the database table into packages based on a predetermined criteria,
for each package:

check consistency for each event contained in the package, the consistency check determining whether relevant context information is provided in each event, apply a consolidation logic to consolidate events contained in the package, wherein the consolidation logic determines whether multiple events invoke a respective service and combines later events of the multiple events into a first event of the multiple events to consolidate invocation of the respective service, determine services operations associated with the consolidated events and each event not being consolidated, and invoke the service operations asynchronously.

* * * * *